US00PP23457P3

(12) United States Plant Patent
Renault

(10) Patent No.: US PP23,457 P3
(45) Date of Patent: Mar. 12, 2013

(54) ***ACTINIDIA DELICIOSA* PLANT NAMED 'RENACT'**

(50) Latin Name: *Actinidia deliciosa*
Varietal Denomination: Renact

(76) Inventor: Jean Renault, Gorron (FR)

( * ) Notice: Subject to any disclaimer, the term of this patent is extended or adjusted under 35 U.S.C. 154(b) by 175 days.

(21) Appl. No.: 12/925,501

(22) Filed: Oct. 21, 2010

(65) Prior Publication Data

US 2012/0102602 P1 Apr. 26, 2012

(51) Int. Cl.
*A01H 5/00* (2006.01)

(52) U.S. Cl. ..... Plt./156

(58) Field of Classification Search ..... Plt./156
See application file for complete search history.

(56) References Cited

PUBLICATIONS

UPOVROM Plant Variety Database Citation for 'Renact' as per QZ PBR20091290; Oct. 15, 2009.*

* cited by examiner

*Primary Examiner* — Kent L Bell
(74) *Attorney, Agent, or Firm* — Cassandra Bright

(57) ABSTRACT

A new and distinct *Actinidia deliciosa* cultivar named 'Renact' is disclosed, characterized by unique self-fertility resulting in fruit of a useful size. The new variety is an *Actinidia deliciosa*, typically useful for home gardening applications.

2 Drawing Sheets

Latin name of the genus and species: *Actinidia deliciosa.*
Variety denomination: 'RENACT'.

BACKGROUND OF THE INVENTION

The new cultivar is a product of a planned breeding program under the direction of the inventor, Jean Renault, a citizen of France. 'Renact' was discovered as a seedling, resulting from an open pollination of the seed parent variety *Actinidia deliciosa* 'Hayward' unpatented. The pollen parent is unknown. 'Renact' was discovered at a commercial nursery in 1995, located in Gorron, France.

The new variety was observed for several years, and first propagated by semi-hardwood cuttings in 2005, at a commercial nursery in Gorron, France. Subsequent evaluations of the variety have shown the characteristics to be true to type.

SUMMARY OF THE INVENTION

Nearly all commercial fruit producing *Actinidia* varieties require a separate male pollinator plant in order to produce fruit of a useful size. 'Renact' was selected for its ability to self-fertilize, with the resulting fruit of a significant size, approximately 70% of the size of 'Hayward' the most commonly grown commercial variety.

The cultivar 'RENACT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RENACT' These characteristics in combination distinguish 'RENACT' as a new and distinct *Actinidia deliciosa* cultivar:

1. Flowers having both complete male and female parts.
2. Self fertilization.
3. Fruits of a good commercial size.

COMPARISON VARIETIES

Plants of the new cultivar 'RENACT' are similar to plants of the seed parent, *Actinidia deliciosa* 'Hayward' in most horticultural characteristics, however, plants of the new cultivar 'RENACT' produce fruit that is approximately 70% of the size of 'Hayward.' Additionally, the new variety is self-fertile whereas 'Hayward' requires a pollinator plant to produce fruit at all, or fruit of any useful size.

Plants of the new cultivar 'RENACT' are similar to plants of the commercial variety, *Actinidia deliciosa* 'Solo', unpatented in most horticultural characteristics, however, plants of the new cultivar 'RENACT' produce larger fruit. Fruit of 'Renact' is both larger than fruit produced by 'Solo' and significantly less pubescent, and of a different shape. The shape of fruit produced by plants of 'Renact' is nearly cylindric, with blunt ends, whereas plants of 'Solo' produce fruit which is elliptic in shape.

BRIEF DESCRIPTION OF THE PHOTOGRAPH

Figure 1:
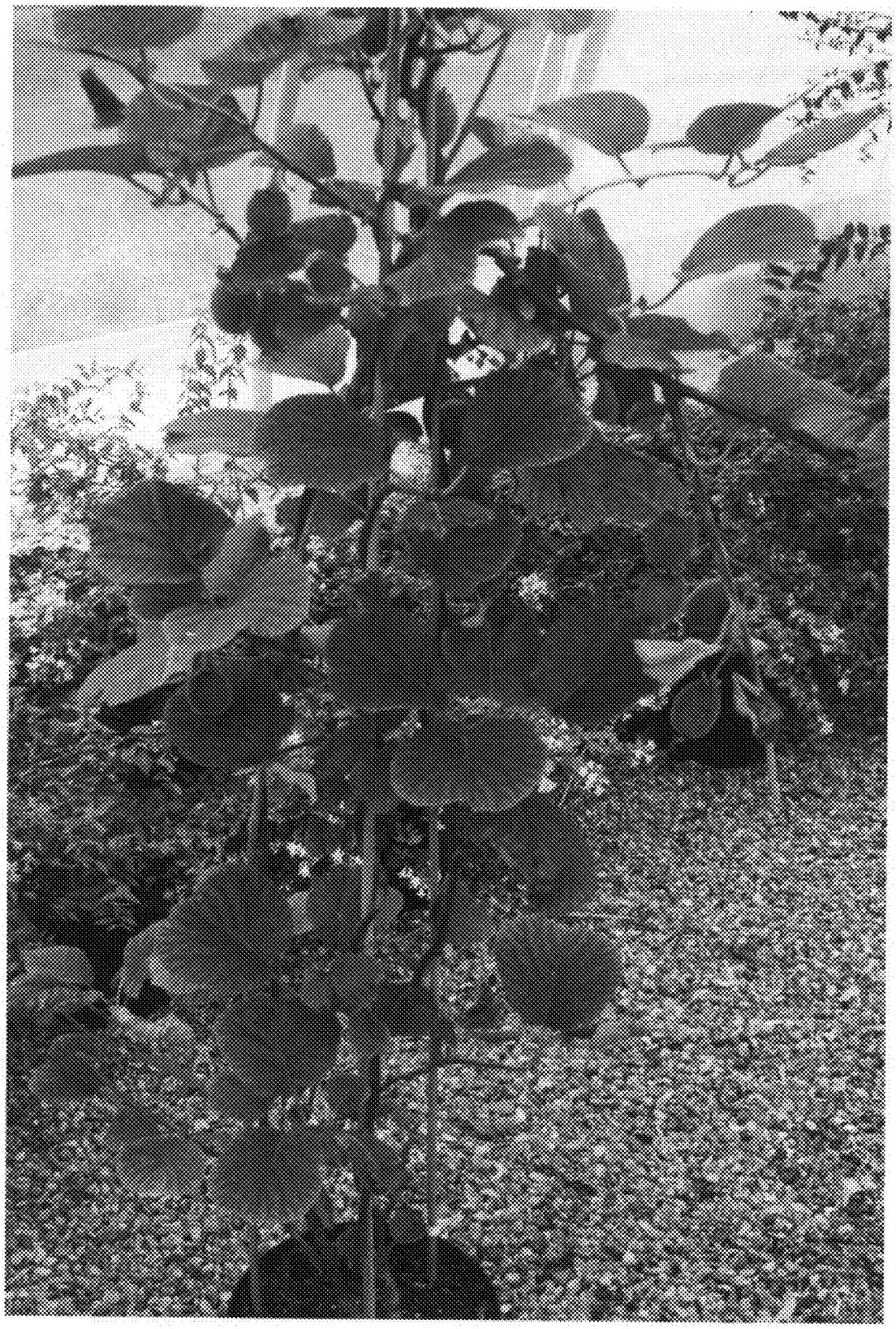

The accompanying photograph in FIG. 1 illustrates in full color a typical plant of 'RENACT' grown in a 10 liter pot, with immature fruit.

Figure 2:
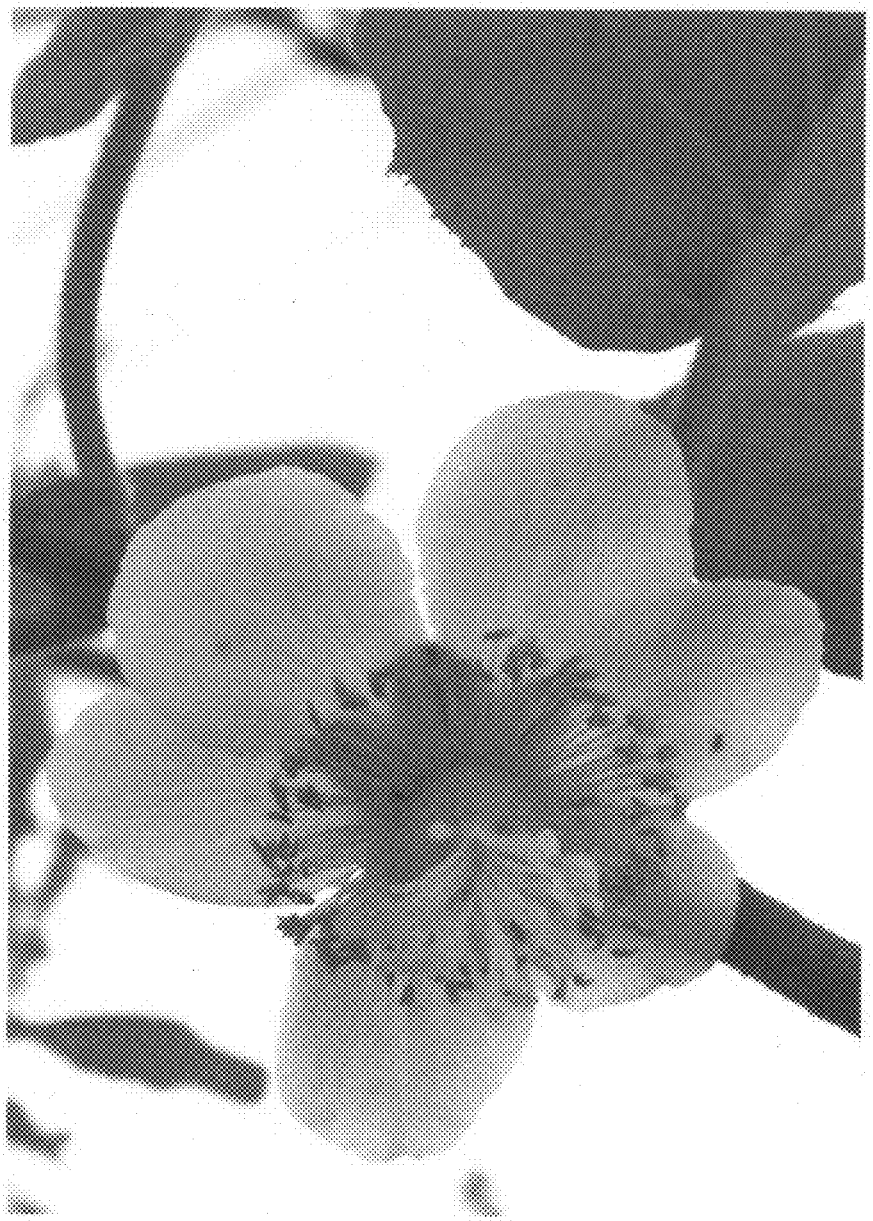

FIG. 2 illustrates in full color typical flowers of 'RENACT'.

All photographs are taken of plants approximately 3 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'RENACT' plants grown outdoors under commercial trial conditions in La Ménitré, France. The growing temperature ranged from approximately 10° C. to 35° C. with infrequent precipitation. Measurements and numerical values represent averages of typical plant types.

Botanical classification: *Actinidia deliciosa* 'RENACT'.

PROPAGATION

Time to initiate roots: Approximately 30 to 35 days at approximately 25° C.

Root description: Fibrous, becoming woody. Typically grown on own roots.

PLANT

Age of the plant described: Approximately 5 years.

Ploidy: Unknown.

Height: Average 2.5 meters, trained on a trellis.

Width: Average 3.0 meters, trained on a trellis.

Vigor: Medium (20 to 30% less than Hayward).

Young shoot color: Near RHS 146 B and 146C both colors present.

Young shoot texture: Pubescent.

Mature stems:

*Stem diameter*.—Average 0.8 to 1.00 cm.

*Stem color*.—Background color near Brown N200B with strong flush near Greyed-Purple N186C.

*Stem texture*.—Heavily lenticeled.

Stem lenticels description: Irregular in shape and size, colored near RHS Greyed-White 156D. Approximately 10 lenticels per square cm.

Trunk diameter: Average 2 cm on a 5 years old plant.

Mature stem length: Approximately 2 meters.

FOLIAGE

Leaf:

*Average length*.—Range between 8 to 12 cm.

*Average width*.—Range between 9 to 15 cm.

*Shape of blade*.—Broadly ovate.

*Apex*.—Subacute or obcordate.

*Base*.—Cordate.

*Attachment*.—Alternate.

*Margin*.—Ciliate.

*Texture of top surface*.—Non pubescent.

*Texture of under side*.—Heavily pubescent, minute, soft hairs.

*Color*.—Mature foliage upper side: Near RHS Yellow-Green 144A. Mature foliage under side: Near RHS Yellow-Green 147 C.

*Petiole*.—Length: Average range 3.5 to 4.5 cm. Diameter: Average 0.45 cm. Texture: Pubescent. Color: Near RHS Yellow-Green 145 C. Closer towards stem attachment, heavily flushed with Greyed-Red 180D. Venation.

*Venation*.—Type: Palmate. Venation color upper side: Near RHS Yellow-Green 144B. Venation color under side: Near RHS Green 143C.

FLOWER

Approximate chilling hours for bud and bloom: 400 to 500 hours.

Flowers per inflorescence: 1 to 3.

*Bud color*.—Near RHS Green-White 157B.

*Bud break color*.—Near RHS Grey-Orange 177 C.

*First flower*.—Fully open flowers begin May-June.

*Flower diameter*.—Average 4 to 5 cm.

*Flower depth*.—Average 2.8 cm.

*Petal quantity*.—6 per flower.

*Petals overlapping*.—Yes.

Petals:

*Length*.—Approximately 2.7 cm.

*Width*.—Approximately 2.6 cm.

*Shape*.—Very broad spatulate.

*Apex*.—Obtuse, rounded.

*Base*.—Truncate.

*Margin*.—Entire.

*Color*.—Upper and lower surfaces: Near RHS White 155D, flushed with Greyed-Orange 170C.

*Quantity of stamens*.—Average 85.

*Filament color*.—Near RHS White 155A.

*Anther color*.—Near RHS Orange-White 159 B when young: change to Greyed-Orange 163B when older.

*Pollen color*.—Near RHS Greyed-Orange 164A.

*Attitude of styles*.—Erect, with slight outward arch.

*Style color*.—Near RHS Green-White 157 D when young, White 155D at maturity.

*Style quantity*.—Average 33.

*Hair on ovary*.—Yes.

*Color of ovary*.—Near RHS Yellow-Green 150C.

*Number of Sepals*.—6.

*Color of sepals, upper and lower surfaces*.—RHS Greyed-Yellow 160A, apex near Greyed-Orange 163B.

*Sepal width*.—Average range 0.5 to 0.8 cm (recurved).

*Sepal length*.—Average range 0.8 to 1 cm.

*Sepal aspect*.—Recurved.

*Sepal texture*.—Pubescent.

Peduncle:

*Length*.—Average range 2.5 to 4 cm.

*Color*.—Near RHS Greyed-Yellow 160 A.

*Texture*.—Pubescent.

Pedicel:

*Length*.—1.5 to 2.0 cm.

*Diameter*.—0.4 cm.

*Color*.—Near RHS Yellow-Green 145A.

*Orientation*.—Nearly completely vertical (10 degrees angle).

*Strength*.—Flexible.

*Texture*.—Pubescent.

FRUIT

Color outer pericarp: Near RHS Yellow 3B.

Color inner pericarp: Near RHS Yellow 3A.

Core color: Near RHS White 155A.

Average weight: Average range 50 to 65 grams.

Length: Avg. 45 mm.

Width: Avg. 35 mm.

Core diameter(average): 10 mm.

Locules:

*Quantity*.—Average 28.

*Length*.—Average 0.6 cm.

*Width*.—Average 0.25 cm.

*Color*.—Near RHS Yellow-Green 145B.

Fruit peduncle length: Average 31.5 mm.

Fruit peduncle width: Average 2 mm.

Fruit peduncle color: Near RHS Greyed-Orange 174A, tinged Greyed-Purple 185A.

General shape: Cylindric.

Stylar end shape: Blunt.

Shoulder shape: Squared.

Calyx ring: Present.
Calyx ring expression: Strong.
Skin color at harvest: Near RHS Grey-Brown 199A.
Hair on fruit skin: Highly pubescent.
Hair adherence to skin: Moderate.
Fruit hair length: Average 0.15 cm.
Skin adherence to flesh at maturity: Moderate.
Fruit core shape: Transversely elliptic.
Core-woody spike: Medium.
Lenticels on fruit: Not present.
Mature seed color: Near Black 202A.
Dried seed: Near Brown 200D.
Harvest time: Mid July.

OTHER CHARACTERISTICS

Disease/pest resistance: Neither resistance nor susceptibility to pathogens and pests common to *Actinidia deliciosa* have been observed.

Temperature tolerance: Tolerates low temperatures to approximately −15° C., tolerates high temperatures to at least 35° C. without negative effects.

What is claimed is:

1. A new and distinct cultivar of *Actinidia deliciosa* plant named 'Renact' as herein illustrated and described.

* * * * *